United States Patent
Wang

(10) Patent No.: US 11,261,477 B2
(45) Date of Patent: Mar. 1, 2022

(54) GLYCOSYLATION MODIFICATION OF BIOACTIVE COMPOUNDS AND DRUGS BY PLANT GLYCOSYLTRANSFERASES (UGTS)

(71) Applicant: UNIVERSITY OF NORTH TEXAS, Denton, TX (US)

(72) Inventor: Xiaoqiang Wang, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 0 days.

(21) Appl. No.: 16/923,986

(22) Filed: Jul. 8, 2020

(65) Prior Publication Data

US 2021/0010056 A1  Jan. 14, 2021

Related U.S. Application Data

(60) Provisional application No. 62/873,620, filed on Jul. 12, 2019.

(51) Int. Cl.
*C12N 9/10* (2006.01)
*C12Q 1/48* (2006.01)

(52) U.S. Cl.
CPC ............. *C12Q 1/48* (2013.01); *C12N 9/1051* (2013.01); *C12Y 204/01017* (2013.01); *G01N 2333/91102* (2013.01)

(58) Field of Classification Search
CPC ........... C12N 9/1051; C12N 9/10; C12Q 1/48
See application file for complete search history.

(56) References Cited

PUBLICATIONS

Kren et al., "Glycosides in Medicine: "The Role of Glycosidic Residue in Biological Activity"" Current Medicinal Chemistry 2001, v 8, p. 1303-1328.
Bowles et al., "Glycosyltransferases: managers of small molecules" Current Opinion in Plant Biology 2005, v 8, p. 254-263.
Shimoda et al., "Synthesis of Oligosaccharides of Genistein and Quercetin as Potential Anti-inflammatory Agents" Chemistry Letters, 2008, v 37, n 8, p. 876-877.
Wang, "Structure, mechanism and engineering of plant natural product glycosyltransferases" FEBS Letters, 2019, 583, p. 3303-3309.
Shao et al., "Crystal Structures of a Multifunctional Triterpene/Flavonoid Glycosyltransferase from Medicago truncatula" The Plant Cell, Nov. 2005.

*Primary Examiner* — Tekchand Saidha
(74) *Attorney, Agent, or Firm* — Greer, Burn & Crain, Ltd.; Gregory P. Einhorn

(57) ABSTRACT

In alternative embodiments, provided are methods for the glycosylation modification of bioactive compounds and drugs using isolated, recombinant or genetically modified uridine diphosphate glycosyl-transferases (UGTs). In alternative embodiments, provided are methods for modifying UGTs to generate recombinant UGTs with altered donor and/or acceptor specificities. In alternative embodiments, provided are methods for screening for recombinantly engineered UGTs with new or altered properties, for example, for new or altered donor and/or acceptor specificities, where in alternative embodiments the screening comprise use of bacterial, yeast or baculovirus expression system.

10 Claims, 2 Drawing Sheets
(2 of 2 Drawing Sheet(s) Filed in Color)

GLYCOSYLATION MODIFICATION OF BIOACTIVE COMPOUNDS AND DRUGS BY PLANT GLYCOSYLTRANSFERASES (UGTS)

RELATED APPLICATIONS

This U.S. utility patent application claims the benefit of priority to U.S. Provisional Patent Application Ser. No. 62/873,620 filed Jul. 12, 2019. The aforementioned application is expressly incorporated herein by reference in its entirety and for all purposes.

TECHNICAL FIELD

This invention generally relates to pharmaceutical drug development and small molecule glycosylation processes. In alternative embodiments, provided are methods for the glycosylation modification of bioactive compounds and drugs using isolated, recombinant or genetically modified uridine diphosphate glycosyl-transferases (UGTs). In alternative embodiments, provided are methods for modifying UGTs to generate recombinant UGTs with altered donor and/or acceptor specificities. In alternative embodiments, provided are methods for screening for recombinantly engineered UGTs with new or altered properties, for example, for new or altered donor and/or acceptor specificities, where in alternative embodiments the screening comprise use of bacterial, yeast or baculovirus expression systems.

BACKGROUND

Glycosylation is a biological process that improves bioavailability and therefore pharmacological activities. The main implication of glycosylation is in drug discovery. Uridine diphosphate (UDP) glycosyltransferases (UGTs) are key components in the glycosylation process. They can be used for modifying small molecular drugs with various sugars.

A major issue in drug modification and discovery is that it is difficult to perform targeted glycosylation of specific drug scaffolds with current conventional synthetic approaches. Different UGTs have unique sequences and specific templates.

The UGT UGT71G1 is a multifunctional glycosyltransferase and can glycosylate terpenoids such as hederagenin, flavonoids such as quercetin, and SN-38, an active metabolite of the anti-cancer drug CPT-11 (irinotecan). Terpenoids have been proven to benefit human health, where some can fight malaria, some can be used to treat cancer.

SUMMARY

In alternative embodiments, provided are methods for designing and generating recombinant or genetically modified uridine diphosphate glycosyl-transferases (UGTs) with modified sequences and compositions complementing target drugs, the method comprising: expressing a recombinant or genetically modified UGT in an *E. coli*, a yeast or a baculovirus expression system.

In alternative embodiments of methods as provided herein, the expressed recombinant or genetically modified UGT has an altered or new donor and/or acceptor specificity, and optionally the recombinant or genetically modified UGT uses UDP-glucuronic acid or UDP-rhamnose as a donor.

In alternative embodiments of methods as provided herein, the expressed recombinant or genetically modified UGT has an altered or new donor and/or acceptor specificity, and optionally the recombinant or genetically modified UGT uses a drug or small molecule as an acceptor, and optionally the acceptor-binding pocket of the UGT is modified.

In alternative embodiments of methods as provided herein, the expressed recombinant or genetically modified UGT has an altered or new donor and/or acceptor specificity, and the method further comprises screening for the new or altered UGT donor and/or acceptor specificity in a bacterial, yeast or baculovirus expression system.

In alternative embodiments, provided are methods for identifying or screening for a recombinant or genetically modified uridine diphosphate glycosyl-transferase (UGT) having a modified sequence such that the modification of the UGT results in the glycosylation of or adding a sugar moiety to an otherwise unglycosylated bioactive compound or target drug, or results in generating a modified glycosylation of a bioactive compound or a target drug by adding a sugar moiety, the method comprising:

(a) providing or having provided a recombinant or genetically modified UGT, wherein the expressed recombinant or genetically modified UGT has an altered or new donor and/or acceptor specificity, (b) providing or having provided an acceptor molecule, (c) expressing the recombinant or genetically modified UGT in an expression system, (d) contacting the recombinant or genetically modified UGT with a bioactive compound or a target drug in the expression system, and (e) screening for the generation of a UGT that results in the glycosylation of an otherwise unglycosylated acceptor molecule, or results in generating a modified glycosylation of the acceptor molecule.

In alternative embodiments of methods as provided herein:

the recombinant or genetically modified UGT uses UDP-glucose, UDP-glucuronic acid and/or UDP-rhamnose as a donor, thereby adding a glucose, glucuronic acid and/or a rhamnose sugar moiety to the acceptor molecule;

the recombinant or genetically modified UGT uses a drug or a small molecule as an acceptor, or the acceptor molecule comprises a drug or a small molecule the acceptor-binding pocket of the recombinant or genetically modified UGT is modified;

the expression system is a cell-based expression system or an in vitro expression system, and the cell-based expression system can comprise a bacterial, a yeast, a baculovirus, or a mammalian expression system;

the UGT is UGT71G1, optionally a *Medicago* UGT71G1;

the acceptor molecule is a terpene, a terpenoid, a flavonoid, an isoflavonoid or a natural product, and optionally the natural product, terpene, terpenoid, flavonoid or isoflavonoid is: ursolic acid, liquiritigenin, 3-Carene; 3,7(11)-Eudesmadiene; 4-Carvomenthenol; 4-Thujanol; alpha-Bergamotene; alpha-Bisabolol, (+)-; alpha-Bulnesene; alpha-Cedrene; alpha-Guaiene; alpha-Ocimene, (3E)-; alpha-Phellandrene; alpha-Pinene; alpha-Terpinene; Aromadendrene; beta-Caryophyllene; beta-Elemene; beta-Farnesene, (6E)-; beta-Ocimene; beta-Pinene; beta-Thujene; Cannabidiol; Cannabigerolic Acid; Carvone, (−)-; Caryophyllene Oxide; Cedrol; cis-2-Pinanol; cis-beta-ocimene; cis-Nerolidol; Citronellol; d-Limonene; delta8-THC; Dronabinol; Eucalyptol; Fenchone; Fenchol; gamma-Elemene; gamma-Terpinene; Geraniol; Geranyl Acetate; Germacrene B; Guaiol; Humulene; (−)-; Isopulegol; Limonene; Linalool; Menthol; Myrcene; Nerol;

Nerolidol; p-Cymene; Phytol; Pulegone; Sabinene; Sabinene Hydrate; Terpineol; Terpinolene; Valencene; (−)-Terpinen-4-ol, (−)-Terpinen-4-ol, d-limonene linalool, 1,8-cineole (eucalyptol), α-pinene, terpineol-4-ol, p-cymene, Δ-3-carene, β-sitosterol, β-myrcene, β-caryophyllene, cannflavin A, apigenin, quercetin, pulegone, borneol; isoborneol; camphene; camphor; delta-3-carene; beta-caryophyllene; caryophyllene oxide; alpha-cedrene; beta-eudesmol; fenchyl alcohol; geraniol; guaiol; alpha-humulene; limonene; linalool; menthol; myrcene; nerol; ocimene; trans-ocimene; alpha-phellandrene; alpha-pinene; beta-pinene; sabinene; alpha-terpinene; alpha-terpineol; terpinolene; alpha-guaiene; elemene; farnesene; germacrene B; guaia-1(10), 11-diene; trans-2-pinanol; selina-3,7(11)-diene; eudesm-7(11)-en-4-ol; valencene; 7,8-dihydroionone, Acetanisole, Acetic Acid, Acetyl Cedrene, Anethole, Anisole, Benzaldehyde, Bergamotene (α-cis-Bergamotene) (α-trans-Bergamotene), Bisabolol (β-Bisabolol), Borneol, Butanoic/Butyric Acid, Cadinene (α-Cadinene) (γ-Cadinene), Cafestol, Caffeic acid, Camphene, Camphor, Capsaicin, Carene (Δ-3-Carene), Carotene, Carvacrol, Carvone, Dextro-Carvone, Laevo-Carvone, Caryophyllene (β-Caryophyllene), Caryophyllene oxide, Castoreum Absolute, Cedrene (α-Cedrene) (β-Cedrene), Cedrene Epoxide (α-Cedrene Epoxide), Cedrol, Cembrene, Chlorogenic Acid, Cinnamaldehyde (α-amyl-Cinnamaldehyde) (α-hexyl-Cinnamaldehyde), Cinnamic Acid, Cinnamyl Alcohol, Citronellal, Citronellol, Cryptone, Curcumene (α-Curcumene) (γ-Curcumene), Decanal, Dehydrovomifoliol, Diallyl Disulfide, Dihydroactinidiolide, Dimethyl Disulfide, Eicosane/lcosane, Elemene (β-Elemene), Estragole, Ethyl acetate, Ethyl Cinnamate, Ethyl maltol, Eucalyptol/1,8-Cineole, Eudesmol (α-Eudesmol) (β-Eudesmol) (γ-Eudesmol), Eugenol, Euphol, Farnesene, Farnesol, Fenchol (β-Fenchol), Fenchone, Geraniol, Geranyl acetate, Germacrenes, Germacrene B, Guaia-1 (10), 1 1-diene, Guaiacol, Guaiene (α-Guaiene), Gurjunene (α-Gurjunene), Herniarin, Hexanaldehyde, Hexanoic Acid, Humulene (α-Humulene) (β-Humulene), Ionol (3-oxo-α-ionol) (β-Ioηol), Ionone (α-Ionone) (β-Ionone), Ipsdienol, Isoamyl acetate, Isoamyl Alcohol, Isoamyl Formate, Isoborneol, Isomyrcenol, Isopulegol, Isovaleric Acid, Isoprene, Kahweol, Lavandulol, Limonene, γ-Linolenic Acid, Linalool, Longifolene, α-Longipinene, Lycopene, Menthol, Methyl butyrate, 3-Mercapto-2-Methylpentanal, Mercaptan/Thiols, β-Mercaptoethanol, Mercaptoacetic Acid, AIM Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (β-Myrcene), γ-Muurolene, Nepetalactone, Nerol, Nerolidol, Neryl acetate, Nonanaldehyde, Nonanoic Acid, Ocimene, Octanal, Octanoic Acid, p-cymene, pentyl butyrate, phellandrene, phenylacetaldehyde, phenylethanethiol, Phenylacetic Acid, Phytol, Pinene, β-Pinene, propanethiol, Pristimerin, Pulegone, Retinol, Rutin, Sabinene, Sabinene Hydrate, cis-Sabinene Hydrate, trans-Sabinene Hydrate, Safranal, α-Selinene, α-Sinensal, β-Sinensal, β-Sitosterol, Squalene, Taxadiene, Terpin hydrate, Terpineol, Terpine-4-ol, α-Terpinene, γ-Terpinene, Terpinolene, Thiophenol, Thujone, Thymol, α-Tocopherol, Tonka Undecanone, Undecanal, Valeraldehyde/Pentanal, Verdoxan, α-Ylangene, Umbelliferone, Vanillin, a phenolic acid, a stilbenoid, a dihydroflavonol, an anthocyanin, an anthocyanidin, a polyphenol, a tannin, a flavone, flavan-3-ol, flavan-4-ol, flavan-3,4-diol flavonol, a stilbenoid, a phytochemicals, an antioxidant, a homoisoflavonoid, a phenylpropanoid, a phloroglucinol coumarin, a phenolic acid, a naphthodianthrone, a steroid glycoside, a bioflavonoid, an isoflavonoid, a neoflavonoid, adenosine, Adhyperforin, amentoflavone, Anandamide, Apigenin, Cannaflavin B, Catechin (C), Catechin 3-gallate (Cg), Chlorogenic acid, cichoric acid, caftaric acid, Daidzein, Delphinidin, Eleutherosides, epicatechin 3-gallate (ECg), Epicatechins, Epicatechin, epigallocatechin, myricetin, Oxalic acid, Pelargonidin, Tannin, Theaflavin-3-gallate, Theanine, Theobromine, Theophylline, Tryptophan, Tyramine, Xanthine, Caffeine, Cannaflavin A, Cannaflavin B, Catechin (C), Catechin 3-gallate (Cg), Epicatechin 3-gallate (ECg), Epicatechins (Epicatechin (EC)), epigallocatechin, Epigallocatechin (EGC), Epigallocatechin 3-gallate (EGCg), Gallocatechin (GC), Gallocatechin 3-gallate (GCg)), Gamma amino butyric acid, Genistein, *Ginkgo biloba*, Ginsenosides, Quercetin, Quercitrin or Rutin;

the recombinant or genetically modified UGT can catalyze a reverse reaction to remove a sugar moiety from a glycosylated bioactive compound or a target drug;

the recombinant or genetically modified UGT is glycosyltransferase UGT78G1 from *Medicago truncatula*, which can catalyze the glycosylation of isoflavonoids and flavonoids, optionally the flavonols kaempferol and myricetin, the isoflavone formononetin, and/or the anthocyanidins pelargonidin and cyanidin;

the recombinant or genetically modified UGT is glycosyltransferase *M. truncatula* UGT72L1, which optionally can produce epicatechin 3'-O-glucoside;

the recombinant or genetically modified UGT is glycosyltransferase *M. truncatula* UGT71G1, which uses UDP-glucose as a sugar donor, and is a multifunctional glycosyltransferase, and optionally has as substrates (can glycosylate) quercetin, genistein, biochanin A, hederagenin, and SN-38 (active metabolite of anticancer drug CPT-11 or irinotecan), and optionally (iso) flavonoids quercetin and genistein as in vitro substrates;

the recombinant or genetically modified UGT is glycosyltransferase UGT85H2, which utilizes UDP-glucose as a donor, and which is a multifunctional (iso)flavonoid glycosyltransferase with activity toward several flavonoid-related secondary metabolites, including isoflavones, flavonols, and chalcone, and optionally has as substrates quercetin; genistein; biochanin A, kaempferol, and isoliquiritigenin;

the recombinant or genetically modified UGT is glycosyltransferase *Medicago* UGT78G1, which utilizes UDP-glucose as a donor, which is an (iso)flavonoid glycosyltransferase with broad activities on isoflavones, optionally formononetin and flavonols, optionally kaempferol, and optionally has activity for the anthocyanidins pelargonidin and cyanidin;

the recombinant or genetically modified UGT is UGT78G1, which can catalyze a reverse reaction to remove a sugar moiety, where the enzyme converts biochanin A 7-O-glucoside, genistein 7-O-glucoside, kaempferol 3-O-glucoside, and quercetin 3-O-glucoside into corresponding aglycones; and optionally UGT78G1 uses quercetin; genistein; Biochanin A, kaempferol; formononetin, daidzein, apigenin, myricetin, pelargonidin and cyanidin as a substrate;

the recombinant or genetically modified UGT is glycosyltransferase UGT88D7, which utilizes UDP-glucuronic acid as a donor, and optionally uses apigenin, baicalein, scutellarein, kaempferol, quercetin and naringenin as a substrate;

the recombinant or genetically modified UGT is glycosyltransferase BpUGT94B1, which utilizes UDP-glucuronic acid as a donor, and optionally uses cyanidin 3-O-glucoside and cyanidin 3-O-6'-O-malonylglucoside as a substrate;

the recombinant or genetically modified UGT is glycosyltransferase UGT89C1, which utilizes UDP-rhamnose as a donor, and optionally uses kaempferol, kae3-O-glucoside and quercetin 3-O-glucoside as a substrate;

the recombinant or genetically modified UGT is glycosyltransferase rice OsCGT, which utilizes UDP-glucose as a donor, and optionally uses phloretin, 2-hydroxyeriodictyol and 2-hydroxynaringenin as a substrate; and/or the recombinant or genetically modified UGT is glycosyltransferase buckwheat FeCGTa (UGT708C1), which utilizes UDP-glucose as a donor, and optionally uses phloretin, 2-hydroxyeriodictyol and 2-hydroxynaringenin as a substrate.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

The drawings set forth herein are illustrative of exemplary embodiments provided herein and are not meant to limit the scope of the invention as encompassed by the claims.

FIG. 1A illustrates the structure of *Medicago* UGT71G1;

FIG. 1B illustrates the structure of donor binding site and interaction between the donor molecule UDP-glucose and the enzyme; a plant UGT specific PSPG signature motif is shown as a ribbon model in yellow; the structure of UDP-glucose is shown as a ball-and-stick model;

FIG. 1C illustrates structures comparing acceptor binding pockets of several plant UGTs including UGT71G1 (dimgrey), UGT78G1 (cyan), VvGT1 (blue), UGT85H2 (orange), and UGT72B1 (lightgrey); catalytic residues are in the UGT71G1 structure; residue numbers in UGT71G1 are labeled, and the UGT72B1 unique long loop (approximately residue 315) is also labeled;

as discussed in detail in Example 1, below.

Figure 2:
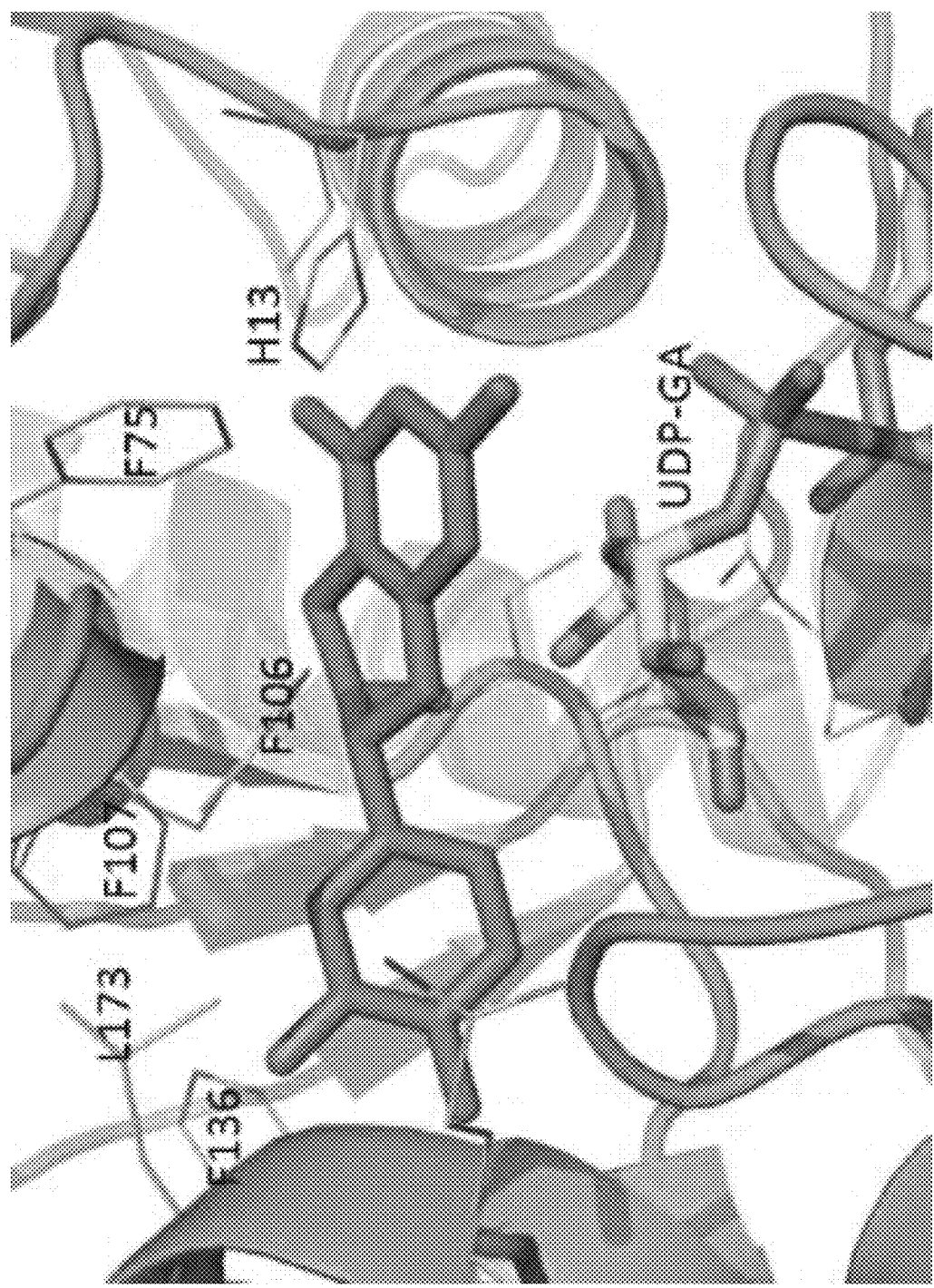

FIG. 2 illustrates a substrate binding pocket of UGT88D7 docked with epicatechin and UDP-glucuronic acid (UDP-GA), as discussed in detail in Example 1, below.

Like reference symbols in the various drawings indicate like elements.

DETAILED DESCRIPTION

In alternative embodiments, provided are methods for the enzymatic glycosylation modification of bioactive compounds and drugs using isolated, recombinant or genetically modified uridine diphosphate glycosyl-transferases (UGTs), where UDP-glucose, UDP-glucuronic acid and/or UDP-rhamnose can be donor molecules, and the acceptor molecule is any small molecule, for example, a terpenoid (e.g., ursolic acid) or a flavonoid (e.g., liquiritigenin) or an isoflavonoid (e.g, genistein). In alternative embodiments, some UGT glycosyltransferases or their mutants also can catalyze a reverse reaction to remove a sugar moiety from a glycosides.

In alternative embodiments, provided are methods for generating chimera UGT enzymes with a modified or genetically engineered acceptor substrate binding pocket complementing with target drug compounds for glycosylation of various drugs with UDP-glucose, UDP-glucuronic acid and/or UDP-rhamnose. For example, the acceptor binding site modification can be based on the UGT78G1 structure, where the acceptor-binding pocket is formed by several helices and loops, and is mainly hydrophobic with many aromatic and other hydrophobic residues, including Phe21, Phe93, Phe202, and Phe374; and has several charged residues in the acceptor-binding pocket, including His26, His155, and Asp376; and His26 acts as a catalytic residue for UGT78G1, and the corresponding histidine acts as a catalytic residue and general base for UGT71G1, VvGT1, and other UGTs; also, an acidic residue, Asp124, forms a hydrogen bond with His26 and also plays an essential role in catalysis.

In alternative embodiments, provided are methods for generating chimera UGT enzymes with a modified or genetically engineered donor binding sites. The donor binding site modification can be based on the UGT78G1 structure, where the UDP donor molecule interacts with a PSPG motif (Trp334-Gln377) in the C-terminal domain of the enzyme; and a uracil ring of the UDP forms parallel π-stacking interactions with the indole ring of Trp334 and forms hydrogen bonds with Ala335 (via its main-chain N and C atoms); and the ribose ring of the UDP molecule forms hydrogen bonds with Gln337 and Glu360; and the a-phosphate group contacts Asn356 and Ser357; and the β-phosphate forms hydrogen bonds with His352. Additionally, Ser308 forms a hydrogen bond with the uracil ring of the UDP molecule, and Thr25 and Ser282 interact with its β-phosphate group.

In alternative embodiments, the UGT is the glycosyltransferase UGT78G1 from *Medicago truncatula*, which an catalyze the glycosylation of various (iso)flavonoids such as the flavonols kaempferol and myricetin, the isoflavone formononetin, and the anthocyanidins pelargonidin and cyanidin.

In alternative embodiments, the UGT is the glycosyltransferase *M. truncatula* UGT72L1, which can produce epicatechin 3'-O-glucoside.

In alternative embodiments, the UGT is the glycosyltransferase *M. truncatula* UGT71G1, which uses UDP-glucose as a sugar donor, and is a multifunctional glycosyltransferase, and has as substrates (can glycosylate) quercetin, genistein, biochanin A, hederagenin, and SN-38 (active metabolite of anti-cancer drug CPT-11 or irinotecan), and (iso)flavonoids such as quercetin and genistein are preferred in vitro substrates.

In alternative embodiments, the UGT is the glycosyltransferase UGT85H2, which utilizes UDP-glucose as a donor, and which is a multifunctional (iso)flavonoid glycosyltransferase with activity toward several flavonoid-related secondary metabolites, including isoflavones, flavonols, and chalcone, and has as substrates quercetin; genistein; biochanin A, kaempferol, and isoliquiritigenin.

In alternative embodiments, the UGT is the glycosyltransferase *Medicago* UGT78G1, which utilizes UDP-glucose as a donor, which is an (iso)flavonoid glycosyltransferase with broad activities toward isoflavones such as formononetin and flavonols such as kaempferol, and also has activity for the anthocyanidins pelargonidin and cyanidin.

In alternative embodiments, UGT78G1 is used to catalyze a reverse reaction to remove a sugar moiety, where the enzyme converts biochanin A 7-O-glucoside, genistein 7-O-glucoside, kaempferol 3-O-glucoside, and quercetin 3-O-glucoside into corresponding aglycones. In alternative embodiments, UGT78G1 uses quercetin; genistein; Biochanin A, kaempferol; formononetin, daidzein, apigenin, myricetin, pelargonidin and cyanidin as a substrate.

In alternative embodiments, the UGT is the glycosyltransferase UGT88D7, which utilizes UDP-glucuronic acid as a donor, and can use apigenin, baicalein, scutellarein, kaempferol, quercetin and naringenin as a substrate.

In alternative embodiments, the UGT is the glycosyltransferase BpUGT94B1, which utilizes UDP-glucuronic acid as a donor, and can use cyanidin 3-O-glucoside and cyanidin 3-O-6'-O-malonylglucoside as a substrate.

In alternative embodiments, the UGT is the glycosyltransferase UGT89C1, which utilizes UDP-rhamnose as a donor, and can use kaempferol, kae3-O-glucoside and quercetin 3-O-glucoside as a substrate.

In alternative embodiments, the UGT is the glycosyltransferase rice OsCGT, which utilizes UDP-glucose as a donor, and can use phloretin, 2-hydroxy-eriodictyol and 2-hydroxynaringenin as a substrate.

In alternative embodiments, the UGT is the glycosyltransferase buckwheat FeCGTa (UGT708C1), which utilizes UDP-glucose as a donor, and can use phloretin, 2-hydroxy-eriodictyol and 2-hydroxynaringenin as a substrate.

In alternative embodiments, provided are methods for making modified or genetically engineered UGTs by manipulating the acceptor binding pocket of the UGT, or by manipulating multiple components of the UGT, where the modifications can be by insertion and deletion, for example, using QUIKCHANGE STRATEGY™ (Stratagene). In alternative embodiments, GT-A, GT-B and GT-C folds of UGTs are modified or genetically engineered to fit desired target compounds.

In alternative embodiments, provided are methods for expressing UGTs, including modified or genetically engineered UGTs, in bacteria such as *E. coli*, or in yeast, baculovirus, mammalian and/or in vitro expression systems. The expressed enzymes can be then purified or isolated by processes comprising use of $Ni^{2+}$-NTA agarose and SUPERDEX-200™ gel filtration, or equivalents.

In alternative embodiments, the purified or isolated modified or genetically engineered UGTs are screened for activity on target compounds such as small molecules, for example, on small molecule drugs. UDP-glucose, UDP-glucuronic acid and/or UDP-rhamnose can be used as the sugar donor substrate. In alternative embodiments, sugar donor specificity is tested. For example, in alternative embodiments, modified or genetically engineered UGTs are screened for specificity for UDP-glucose, UDP-glucuronic acid and/or UDP-rhamnose as the sugar donor molecule. In alternative embodiments, modified or genetically engineered UGTs are screened for their ability to modify different small molecules such as flavonoids or small molecule drug by glycosylation with UDP-glucose, UDP-glucuronic acid and/or UDP-rhamnose.

In alternative embodiments, LC-MS and NMR analysis are used before, during and/or after the screening reaction, for example, LC-MS and NMR analysis are used before purification of the reaction products from enzyme assays with the bacterial-, yeast- or baculovirus-expressed modified or genetically engineered UGT. In alternative embodiments, expressed recombinant or genetically modified UGT has an altered or new donor and/or acceptor specificity, and methods as provided herein comprise screening for the new or altered UGT donor and/or acceptor specificity in a bacterial, yeast, baculovirus, mammalian or in vitro expression system. In alternative embodiments, any bacterial, yeast, baculovirus, mammalian or in vitro expression system can be used, for example, as described in U.S. Pat. Nos. 9,909,106; 10,017,783; 10,172,931; 10,344,288; 10,294,484; and U.S. patent application publications nos. 20180127728; 20180087070; 20190092838.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Methods and Engineered Enzymes for the Glycosylation of Bioactive Compounds and Drugs with Various Sugar Donors Based on *Medicago truncatula* UGT structures we determined previously, molecular modeling and docking based enzyme design is performed to generate novel biocatalysts for glycosylation of drugs with various sugar donors. In alternative embodiments, UGT88D7 and BpUGT94B1, which utilize UDP-glucuronic acid, and UGT89C1 which recognizes UDP-rhamnose, are designed and engineered. UGT71G1 exhibited very broad substrate specificity for glucosylation, and will also be a mutation template to change its sugar specificity for other types of sugars, such as UDP-glucuronic acid and UDP-rhamnose. The newly generated UGT biocatalysts are used for glycosylation modification of various bioactive compounds and drugs.

C-Glycosylation of Bioactive Compounds and Drugs

C-glycosides may be more important in pharmacological activity, but their chemical synthesis is even more difficult. So far, there are several C-GTs identified in plants, e.g., rice OsCGT, and buckwheat FeCGTa, and these CGTs only recognize flavonoids. Molecular modeling is performed and docking based enzyme design is used to generate novel CGT biocatalysts for glycosylation of various bioactive compounds and drugs. Also, these C-GTs are engineered to manipulate their sugar specificity and utilize other types of sugars for the glycosylation modification of drugs.

Glycosylation is the reaction to transfer sugars from donor molecules to various acceptor molecules including macromolecules and small molecules such as natural products. It is a key mechanism in determining chemical complexity and diversity of small molecular natural products and bioactive compounds (1). Glycosylation often enhances solubility, stability and bioactivity, often also reducing toxicity. Glycosylation can improve bioavailability and pharmacological activities with implications in drug discovery. So it is significant and valuable to glycosylate the bioactive compounds and drugs for drug discovery or reducing drugs' toxicity or improving their bioactivity and bioavailability.

For example, quercetin is a valuable bioactive flavonoid with antioxidant activity. Quercetin may be decorated with different sugars to have different activities. Quercetin-7-glucuronide with sugar glucuronic acid in 7-OH position is a more efficient antioxidant (2). Ivermectin is a medication used to treat many types of parasite infestations, and a glycoside modified with sugars. Glycyrrhizin is a sweetener, 50-100 times sweeter than sucrose, and is a triterpene glycoside attached with sugars.

Catechin and epicatechin can be glucuronosylated by mammalian glucuronosyltransferases to have enhanced brain bioavailability, and catechin and epicatechin glucuronides were detected in rat brain and associated with alleviation of the development of Alzheimers' symptoms (3) and attenuation of features of metabolic syndrome (4).

Uridine diphosphate glycosyltransferases (UGTs), members of family 1 of the glycosyltransferase superfamily, are the central players for the glycosylation of small molecules (5). In human, there are 27 UGT sequences identified, and these UGTs are key phase II drug metabolizing enzymes and play central roles in metabolism and detoxification of foreign chemicals such as carcinogens and hydrophobic drugs (6). In plants, a large number of UGTs have evolved for the glycosylation of plant natural products, e.g. 107 UGTs have been identified in *Arabidopsis thaliana* (7), and over 300 UGTs are also present in a model legume *Medicago truncatula* and other plant species. Glycosylation mediated by UGTs is one of the major factors determining natural product bioactivity and bioavailability (8)(9). UGTs have attracted extensive research interest due to their physiological functions and their potential application inbiotechnology.

UGT Structures:

We determined crystal structures of three plant UGTs, including *Medicago truncatula* UGT71G1, UGT85H2, and UGT78G1 (see FIG. 1A-C) (10) (11) (12). UGT71G1 is a multifunctional triterpene/flavonoid glycosyltransferase (13), UGT85H2 and UGT78G1 are (iso)flavonoid glycosyltransferases (14). They all prefer UDP-glucose as sugar donor to transfer glucose to small molecules and produce glucosides. These studies provided the first structural insights into UGTs and the glycosylation mechanism of small molecules, and revealed detailed interactions between enzyme and substrates including sugar donor and acceptor (FIG. 1B-C). Structure-based mutagenesis studies on UGT71G1 and UGT85H2 showed that we were able to manipulate the regio-selectivity of glycosylation, and improve the enzyme activity and quality by site-directed mutations (15)(16).

Figure 1A:
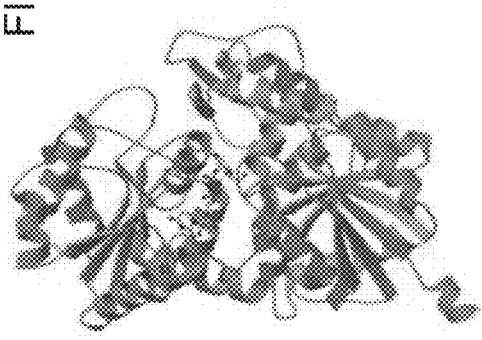
FIG. 1A-C illustrate images of crystal structures of three plant UGTs.
Figure 1B:
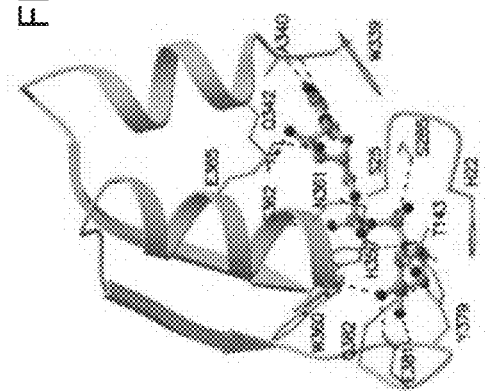
Figure 1C:
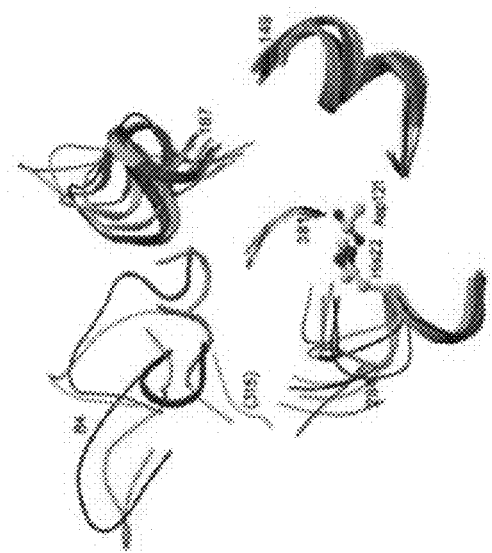

FIG. 1A-C illustrate images of crystal structures of three plant UGTs:

FIG. 1A illustrates the structure of *Medicago* UGT71G1; the structure consists of two similar N- and C-terminal domains, and the active site is located in a deep cleft between the two domains;

FIG. 1B illustrates the structure of donor binding site and interaction between the donor molecule UDP-glucose and the enzyme; a plant UGT specific PSPG signature motif is shown as a ribbon model in yellow; the structure of UDP-glucose is shown as a ball-and-stick model;

FIG. 1C illustrates structures comparing acceptor binding pockets of several plant UGTs including UGT71G1 (dimgrey), UGT78G1 (cyan), VvGT1 (blue), UGT85H2 (orange), and UGT72B1 (lightgrey); catalytic residues are in the UGT71G1 structure; residue numbers in UGT71G1 are labeled, and the UGT72B1 unique long loop (approximately residue 315) is also labeled.

Modification of bioactive compounds and drugs with plant UGTs and their mutants: The UGT structural studies showed that different UGTs have quite different sequences in their substrate binding pockets including the length and composition of amino acids for recognizing various acceptor substrates (FIG. 1C). We utilize plant UGTs and their mutants for glycosylation modification of bioactive compounds and drugs.

Glycosylation modification of bioactive compounds and drugs with UGT71G1 and other UGTs: UGT71G1 can glycosylate terpenoids (e.g., hederagenin), flavonoids (e.g., quercetin), and SN-38 (active metabolite of anti-cancer drug CPT-11 or irinotecan). Many terpenoids and flavonoids are bioactive compounds and drugs with significant benefits for human health. For example, terpenoid artemisinin is an anti-malarial drug. Taxol is also a terpenoid compound and the most well-known natural-source cancer drug. Phenoxodiol is an isoflavonoid derivative and a new oncological agent.

UGT71G1 has a relatively large acceptor substrate binding pocket and may recognize many other small molecules. We utilize UGT71G1 and other UGTs, including recombinantly modified forms, as biocatalysts for glycosylation modification of various drugs.

Design and engineer UGTs as novel biocatalysts for glycosylation of drugs: We also design UGT mutants by manipulating the acceptor substrate binding pocket (FIG. 1C), including single mutation on acceptor binding pocket, multiple mutation, and insertion and deletion mutation. We generate chimera UGT biocatalysts with an acceptor substrate binding pocket complementing with target drug compounds, for glycosylation of various drugs with UDP-glucose.

Mutant generation, expression and purification: In alternative embodiments, Mutants of UGT71G1 and other UGTs are constructed using the QUIKCHANGE™ (QuikChange) strategy (Stratagene). In alternative embodiments, all UGTs and their mutants are expressed and purified according to established methods, e.g., see reference (10). Briefly, in alternative embodiments, UGTs and their mutants are expressed in *E. coli* BL21(DE3) cells. The target proteins can be purified with $Ni^{+2}$-NTA agarose and SUPERDEX-200™ gel filtration column.

Production of glycosylated drugs—Enzyme assays: In alternative embodiments, enzyme assays are performed essentially according to the method as described e.g., in reference (10). In alternative embodiments, the target drugs and bioactive compounds (e.g., catechin, epicatechin) are used as substrates for these UGTs and their mutants. UDP-glucose can be used as sugar donor substrate. In alternative embodiments, the reaction mixtures are then subjected to analysis, e.g., LC-MS and NMR analysis, and/or the glycosylated drugs can be purified.

Production of glycosylated drugs—Bacterial whole-cell UGT mediated glycosylation: In alternative embodiments, bacterial whole-cell UGT mediated glycosylation is carried out for glycosylation of drugs, e.g., according to an established method as set forth in references (17), (18). In alternative embodiments, *E. coli* strains carrying the UGT mutants are grown in Terrific Broth (TB) at 37° C. When the $OD_{600}$ nm of the bacterial culture reaches 0.7, 0.1 mM substrates, and UDP-glucose are added into the culture followed by the addition of 0.1 mM isopropyl-1-thio-h-D-galactopyranoside. In alternative embodiments, the culture is incubated for 24 h at 20° C., the medium and bacterial cells are separated by centrifugation e.g., for 30 min at 4,000×g at 4° C. In alternative embodiments, the medium is acidified with 6 N HCl to pH 1, extracted twice with ethyl acetate, and dried under nitrogen gas, and the products can be analyzed e.g., by HPLC.

Glycosylation of Bioactive Compounds and Drugs with Various Sugar Donors

Modification of Drugs with Various Sugars by Utilizing Novel UGTs

UGT71G1 utilizes UDP-glucose as sugar donor substrate, UGT88D7 and BpUGT94B1 utilize UDP-glucuronic acid, and UGT89C1 recognizes UDP-rhamnose. We obtained UGT88D7, BpUGT94B1 and UGT89C1 by gene synthesis. These UGTs are utilized to modify drugs with different sugars, e.g., glucuronic acid and rhamnose.

Design and Engineer UDP-Glucuronic Acid Specific UGT Mutants for Modification of Drugs with UDP-Glucuronic Acid Based on *Medicago truncatula* UGT structures previously determined, and sequence alignment analysis, UGT88D7 and BpUGT94B1 are molecularly modeled to generate their three dimensional structural models, using e.g., the program MODELLER™ (19), and energy minimization and molecular dynamics simulations are performed, e.g., with the programs CHIMERA (20) and CHARMM (21).

In alternative embodiments, docking studies with bioactive compounds and drugs are conducted, e.g., manually, e.g., with the program COOT™ (22) or automatically using the program AUTODOCK™ (23) to predict the interactions between enzymes and the desired substrates, for example, for Lamiales UGT88D7, which recognizes flavonoids such as apigenin. In alternative embodiments, mutants are designed with high activity toward target drug compounds by removing possible stereochemical hindrance and enhancing their interactions.

UGT88D7 is 33% identical to UGT71G1, and a structural model of UGT88D7 was generated using UGT71G1 structure; this is also the best template for UGT88D7 modeling. UDP-glucuronic acid was modeled according to the conformation and location of UDP-glucose in the structure of UGT71G1. Epicatechin, an example of target bioactive compounds, was docketed into the enzyme active site with its 5-OH appropriately oriented toward the catalytic residue His13 and close to UDP-glucuronic acid (FIG. 2). The substrate binding pocket contains several large hydrophobic residues, i.e., Phe 75, Phe 106, Phe 107, and Phe 136, indicating some potential stereochemical hindrance problems. This analysis helps us identify potential residues for mutation to better complement the target bioactive compounds and drugs, and also enhance the enzyme-ligand interactions. In alternative embodiments, UGT88D7 mutants are designed for glucuronidation of the target bioactive compounds and drugs. Single or multiple amino acids interacting with acceptor substrates are selected to design mutants for altering pocket topology, including size and composition.

FIG. 2 illustrates a substrate binding pocket of UGT88D7 docked with epicatechin and UDP-glucuronic acid (UDP-GA).

BpUGT94B1 is a sugar-sugar/branch forming glucuronosyltransferase to catalyze glucuronidation of a sugar already attached to flavonoid such as cyanidin (24). In alternative embodiments, modeling and docking studies are similarly performed for BpUGT94B1 for design of mutants to produce disaccharide glucuronides of bioactive compounds and drugs.

Design and Engineer UDP-Rhamnose Specific UGT for Modification of Drugs with UDP-Rhamnose UGT89C1 recognizes UDP-rhamnose as sugar donor substrate, and is mainly active toward flavonoids. In alternative embodiments, using approaches similar to those as described above for UDP-glucuronic acid specific UGT modeling and design, UGT89C1 mutants for glycosylation of target bioactive compounds and drugs with UDP-rhamnose are designed and generated.

Design and Engineer UGT71G1 for Manipulation of Donor Specificity Toward Modification of Drugs with Various Sugars UGT71G1 exhibited very broad substrate specificity for glucosylation of various bioactive compounds with UDP-glucose, and will be a major mutation template to change its sugar specificity for other types of sugars.

Key amino acids and structural features for UDP-glucuronic acid specific UGT have been reported. Studies of UGT89C1 and UDP-rhamnose specificity are also reported. In alternative embodiments, these key amino acids and structural features are introduced into UGT71G1 to design and generate novel UGT71G1 mutants with sugar donor specificity for UDP-glucuronic acid or UDP-rhamnose.

In alternative embodiments, modeling and docking studies of UGT71G1 mutants with the target drug compounds are carried out to design and generate more mutations to allow the target compounds fit the mutants' substrate binding pocket well. These novel mutants are designed to recognize new sugar donors and also have activity on the target drug compounds.

Mutant generation, expression and purification: In alternative embodiments, mutants of target UGTs are constructed, and the enzymes are expressed and purified, e.g., using approaches similar to those as described above, e.g., using a bacterial, a yeast, a baculovirus or a mammalian cell-based, or in vitro, expression system.

Production of glycosylated drugs—Enzyme assay: In alternative embodiments, enzyme assays are performed using approaches similar to those as described above. In alternative embodiments, UDP-glucuronic acid and UDP-rhamnose are be used as sugar donor substrates for UDP-glucuronic acid and UDP-rhamnose specific UGTs, respectively.

Production of glycosylated drugs—Bacterial whole-cell UGT mediated glycosylation: Bacterial whole-cell UGT mediated glycosylation are carried out to produce glycosides, e.g., using approaches similar to those as described above, e.g., using *E. coli* or yeast or a baculovirus systems. In alternative embodiments, for glucuronidation, an engineered *E. coli* strain that can accumulate UDP-glucuronic acid by deleting the araA gene encoding UDP-4-deoxy-4-formamido-L-arabinose formyltransferase/UDP-glucuronic acid C-4" decarboxylase that use UDP-glucuronic acid as a substrate is used (25). This *E. coli* accumulating UDP-glucuronic acid are transformed with the active glucuronosyltransferase mutants for production of glucuronides.

C-glycosylation of bioactive compounds and drugs: Glycosylation often occurs on oxygen atoms, UGT71G1 and other target UGTs above are all involved in the O-glycosylation. C-glycosylation also occurs, and many C-glycosides are identified, such as C-glycosyl flavones maysin and apimaysin from corn (26); apigenin 6-C-glucosyl-8-arabinoside (schaftoside), apigenin 6-C-arabinosyl-8-C-glucoside (isoschaftoside), luteolin 8-C-glucoside (orientin) and luteolin 6-C-glucoside (isoorientin) detected in tea (27); and daidzein 8-C-glucoside (puerarin) from kudzu. Puerarin has anticonvulsive, antidipsotropic activity and protective effect on diabetic retinopathy (28). C-glycosides are very stable since their C—C bonds are resistant to glycosidase or acid hydrolysis, and may be more important in pharmacological activity.

Several C-GTs have been identified in several plant species, including OsCGT from rice (*Oryza sativa*)(29), GtUF6CGT1 from Japanese gentian (*Gentiana triflora*) (30), MiCGT which is a novel benzophenone C-glycosyltransferase from *Mangifera indica*(31), FeCGTa (UGT708C1) and FeCGTb (UGT708C2) from *Fagopyrum esculentum* M. (buckwheat)(32), and a 2-hydroxyflavanone C-glucosyltransferase (UGT708D1) from soybean(33). These C-GTs utilize UDP-glucose as sugar donor, and catalyze the C-glycosylation of flavonoids. As described above, some key amino acids and structural features have been identified, e.g., key arginines (Arg25 in red daisy BpUGT94B1, Arg350 in Lamiales F7GAT UGT88D7) can interact with anionic carboxylate of the glucuronic acid as the key requirement for sugar specificity of UDP-glucuronic acid. We obtained OsCGT and FeCGT by gene synthesis. In alternative embodiments, these C-GTs are genetically engineered to change their sugar and acceptor specificity toward C-glycosylation of drugs.

Manipulation of acceptor specificity for C-glycosylating drugs: In alternative embodiments, molecular modeling studies of these C-GTs is conducted using the structures of UGT71G1 and other known UGT structures as templates. In alternative embodiments, the substrate binding pocket of these C-GTs are modified to complement the target drug compounds and to effect the C-glucosylation of drugs.

Manipulation of donor specificity for C-glycosylating drugs: These C-GTs recognize UDP-glucose for glycosylation. In alternative embodiments, key amino acids and structural features for UDP-glucuronic acid or UDP-rhamnose are modified. In alternative embodiments, C-GT mutants are molecularly modeled and designed to have different sugar donor specificity such that they can modify their target drug compounds with different sugars.

Mutant generation and activity assays for production of C-glycosylated drugs: Rice OsCGT and buckwheat FeCGTa are obtained by gene synthesis. All C-GT mutants can be constructed using the QUIKCHANGE™ strategy (Stratagene), and expressed and purified according to established methods. In alternative embodiments, enzyme assays are performed, e.g., using established methods e.g., as described in reference (10). Bacterial whole-cell UGT mediated C-glycosylation can be carried out to produce C-glycosides as described herein.

REFERENCES

1. X. Wang, Structure, mechanism and engineering of plant natural product glycosyltransferases. *FEBS Lett.* 583, 3303-3309 (2009).
2. K. M. Janisch Williamson, G., Needs, P., Plumb, G. W., Properties of quercetin conjugates: modulation of LDL oxidation and binding to human serum albumin. *Free Radic Res.* 38, 877-884 (2004).

3. J. Wang et al., Brain-targeted proanthocyanidin metabolites for Alzheimer's disease treatment. *J. Neurosci.* 32, 5144-5150(2012).
4. J. Wang et al., Role of standardized grape polyphenol preparation as a novel treatment to improve synaptic plasticity through attenuation of features of metabolic syndrome in a mouse model. *Mol Nutr Food Res.* 57, 2091-2102 (2013).
5. D. Bowles, E. K. Lim, B. Poppenberger, F. E. Vaistij, Glycosyltransferases of lipophilic small molecules. *Annu. Rev. Plant Biol.* 57, 567-597 (2006).
6. C. Guillemette, Pharmacogenomics of human UDP-glucuronosyltransferase enzymes. *Pharmacogenomics J.* 3, 136-158 (2003).
7. Y. Li, S. Baldauf, E. K. Lim, D. J. Bowles, Phylogenetic analysis of the UDP-glycosyltransferase multigene family of *Arabidopsis thaliana*. *J. Biol. Chem.* 276, 4338-4343 (2001).
8. D. Bowles, J. Isayenkova, E. Lim, B. Poppenberger, Glycosyltransferases: managers of small molecules. *Curr. Opin. Plant Biol.* 8, 254-263 (2005).
9. V. Kren, L. Martinkova, L. Martinková, Glycosides in medicine: "The role of glycosidic residue in biological activity." *Curr Med Chem.* 8, 1303-1308 (2001).
10. H. Shao et al., Crystal structures of a multifunctional triterpene/flavonoid glycosyltransferase from *Medicago truncatula*. *Plant Cell.* 17, 3141-3154 (2005).
11. L. Li et al., Crystal structure of *Medicago truncatula* UGT85H2—Insights into the structural basis of a multifunctional (iso)flavonoid glycosyltransferase. *J. Mol. Biol.* 370, 951-963 (2007).
12. L. V Modolo, L. Li, R. A. Dixon, X. Wang, Crystal structures of glycosyltransferase UGT78G1 reveal the molecular basis for glycosylation and deglycosylation of (iso)flavonoids. *J. Mol. Biol.* 392, 1292-1302 (2009).
13. L. Achnine et al., Genomics-based selection and functional characterization of triterpene glycosyltransferases from the model legume *Medicago truncatula*. *Plant J.* 41, 875-887 (2005).
14. L. V Modolo et al., A functional genomics approach to (iso)flavonoid glycosylation in the model legume *Medicago truncatula*. *Plant Mol Biol.* 64, 499-518 (2007).
15. X. He, X. Wang, R. A. Dixon, Mutational analysis of the *Medicago* glycosyltransferase UGT71G1 reveals residues that control regioselectivity for (iso)flavonoid glycosylation. *J. Biol. Chem.* 281, 34441-34447 (2006).
16. L. V Modolo, E.-T. L. L., R. A. Dixon, X. Wang, Single amino acid mutations of *Medicago* glycosyltransferase UGT85H2 enhance activity and impart reversibility. *FEBS Lett.* 583, 2131-2135 (2009).
17. E. K. Lim, D. A. Ashford, B. Hou, R. G. Jackson, D. J. Bowles, *Arabidopsis* glycosyltransferases as biocatalysts in fermentation for regioselective synthesis of diverse quercetin glucosides. *Biotech. Bioeng.* 87, 623-631 (2004).
18. X. He, W. Li, J. W. Blount, R. A. Dixon, Regioselective synthesis of plant (iso)flavone glycosides in *Escherichia coli*. *Appl Microbiol Biotechnol.* 80, 253-260 (2008).
19. A. Fiser, A. Sali, in *Methods in Enzymology*, C. W. Carter, R. M. Sweet, Eds. (Academic Press, San Diego, 2003), vol. 374, pp. 463-493.
20. C. C. Huang Couch, G. S., Pettersen, E. F., and Ferrin, T. E, Chimera: An Extensible Molecular Modeling Application Constructed Using Standard Components. *Pacific Symp. Biocomput.* 1, 724 (1996).
21. B. R. Brooks et al., CHARMM: A Program for Macromolecular Energy, Minimization, and Dynamics Calculations. *J. Comp. Chem.* 4, 187-217 (1983).
22. P. Emsley, K. Cowtan, Coot: model-building tools for molecular graphics. *Acta Crystallogr. D.* 60, 2126-2132 (2004).
23. G. M. Morris et al., Autodock4 and AutoDockTools4: automated docking with selective receptor flexiblity. *J. Comput. Chem.* 16, 2785-2791 (2009).
24. S. A. Osmani, S. Bak, A. Imberty, C. E. Olsen, B. L. Moller, Catalytic key amino acids and UDP-sugar donor specificity of a plant glucuronosyltransferase, UGT94B1: molecular modeling substantiated by site-specific mutagenesis and biochemical analyses. *Plant Physiol.* 148, 1295-1308 (2008).
25. J. H. Kim, S. Y., Lee, H. R., Park, K. S., Kim, B. G., & Ahn, Metabolic engineering of *Escherichia coli* for the biosynthesis of flavonoid-O-glucuronides and flavonoid-O-galactoside. *Appl. Microbiol. Biotechnol.* 99, 2233-2242 (2015).
26. M. Cortés-Cruz Snook, M., McMullen, M. D., The genetic basis of C-glycosyl flavone B-ring modification in maize (*Zea mays* L.) silks. *Genome Biol.* 46, 182-194 (2003).
27. U. H. Engelhardt Finger, A., Kuhr, S., Determination of flavone C-glycosides in tea. *Z Leb. Unters Forsch.* 197, 239-244 (1993).
28. Y. Teng Cui, H., Yang, M., Song, H., Zhang, Q., Su, Y., Zheng, J., Protective effect of puerarin on diabetic retinopathy in rats. *Mol Biol Rep.* 36, 1129-1133 (2009).
29. M. Brazier-Hicks et al., The C-glycosylation of flavonoids in cereals. *J Biol Chem.* 284, 17926-17934 (2009).
30. N. Sasaki et al., Identification of the glucosyltransferase that mediates direct flavone C-glucosylation in *Gentiana triflora*. *FEBS Lett.* 589, 182-187(2015).
31. D. Chen et al., Probing the Catalytic Promiscuity of a Regio- and Stereospecific C-Glycosyltransferase from *Mangifera indica*. *Angew Chem Int Ed Engl.* 54, 12678-12682 (2015).
32. Y. Nagatomo et al., Purification, molecular cloning and functional characterization of flavonoid C-glucosyltransferases from *Fagopyrum esculentum* M. (buckwheat) cotyledon. *Plant J.* 80, 437-448 (2014).
33. Y. Hirade et al., Identification and functional analysis of 2-hydroxyflavanone C-glucosyltransferase in soybean (*Glycine max*). *FEBS Lett.* 589, 1778-1786 (2015).

A number of embodiments of the invention have been described. Nevertheless, it can be understood that various modifications may be made without departing from the spirit and scope of the invention. Accordingly, other embodiments are within the scope of the following claims.

What is claimed is:

1. A method for identifying or screening for a recombinant or genetically modified uridine diphosphate glycosyl-transferase (UGT) having a modified sequence such that the modification of the UGT results in the glycosylation of or adding a sugar moiety to an otherwise unglycosylated bioactive compound or target drug, or results in generating a modified glycosylation of a bioactive compound or a target drug by adding a sugar moiety, the method comprising:
    (a) providing or having provided a recombinant or genetically modified UGT comprising a *M. truncatula* uridine diphosphate glycosyl-transferase (UGT) UGT71G1, wherein the expressed recombinant or genetically modified UGT has an altered or new donor and/or acceptor specificity, (b) providing or having provided an acceptor molecule,
(c) expressing the recombinant or genetically modified UGT in an expression system,
(d) contacting the recombinant or genetically modified UGT with a bioactive compound or a target drug in the expression system, and
(e) screening for the generation of a UGT that results in the glycosylation of an otherwise unglycosylated acceptor molecule, or results in generating a modified glycosylation of the acceptor molecule.

2. The method of claim 1, wherein the recombinant or genetically modified UGT uses UDP-glucose, UDP-glucuronic acid and/or UDP-rhamnose as a donor, thereby adding a glucose, glucuronic acid and/or a rhamnose sugar moiety to the acceptor molecule.

3. The method of claim 1, wherein the recombinant or genetically modified UGT uses a drug or a small molecule as an acceptor, or the acceptor molecule comprises a drug or a small molecule.

4. The method of claim 1, wherein the acceptor-binding pocket of the recombinant or genetically modified UGT is modified.

5. The method of claim 1, wherein the expression system is a cell-based expression system or an in vitro expression system.

6. The method of claim 5, wherein the cell-based expression system comprises a bacterial, a yeast, a baculovirus or a mammalian cell-based expression system.

7. The method of claim 1, wherein the acceptor molecule is a terpene, a terpenoid, a flavonoid, an isoflavonoid or a natural product.

8. The method of claim 7, wherein the natural product, terpene, terpenoid, flavonoid or isoflavonoid is: ursolic acid, liquiritigenin, 3-Carene; 3,7(11)-Eudesmadiene; 4-Carvomenthenol; 4-Thujanol; alpha-Bergamotene; alpha-Bisabolol, (+)-; alpha-Bulnesene; alpha-Cedrene; alpha-Guaiene; alpha-Ocimene, (3E)-; alpha-Phellandrene; alpha-Pinene; alpha-Terpinene; Aromadendrene; beta-Caryophyllene; beta-Elemene; beta-Farnesene, (6E)-; beta-Ocimene; beta-Pinene; beta-Thujene; Cannabidiol; Cannabigerolic Acid; Carvone, (−)-; Caryophyllene Oxide; Cedrol; cis-2-Pinanol; cis-beta-ocimene; cis-Nerolidol; Citronellol; d-Limonene; delta8-THC; Dronabinol; Eucalyptol; Fenchone; Fenchol; gamma-Elemene; gamma-Terpinene; Geraniol; Geranyl Acetate; Germacrene B; Guaiol; Humulene; (−)-; Isopulegol; Limonene; Linalool; Menthol; Myrcene; Nerol; Nerolidol; p-Cymene; Phytol; Pulegone; Sabinene; Sabinene Hydrate; Terpineol; Terpinolene; Valencene; (−)-Terpinen-4-ol, (−)-Terpinen-4-ol, d-limonene linalool, 1,8-cineole (eucalyptol), α-pinene, terpineol-4-ol, p-cymene, Δ-3-carene, β-sitosterol, β-myrcene, β-caryophyllene, cannflavin A, apigenin, quercetin, pulegone, borneol; isoborneol; camphene; camphor; delta-3-carene; beta-caryophyllene; caryophyllene oxide; alpha-cedrene; beta-eudesmol; fenchyl alcohol; geraniol; guaiol; alpha-humulene; limonene; linalool; menthol; myrcene; nerol; ocimene; trans-ocimene; alpha-phellandrene; alpha-pinene; beta-pinene; sabinene; alpha-terpinene; alpha-terpineol; terpinolene; alpha-guaiene; elemene; farnesene; germacrene B; guaia-1(10), 11-diene; trans-2-pinanol; selina-3,7(11)-diene; eudesm-7(11)-en-4-ol; valencene; 7,8-dihydroionone, Acetanisole, Acetic Acid, Acetyl Cedrene, Anethole, Anisole, Benzaldehyde, Bergamotene (α-cis-Bergamotene) (α-trans-Bergamotene), Bisabolol (β-Bisabolol), Borneol, Butanoic/Butyric Acid, Cadinene (α-Cadinene) (γ-Cadinene), Cafestol, Caffeic acid, Camphene, Camphor, Capsaicin, Carene (Δ-3-Carene), Carotene, Carvacrol, Carvone, Dextro-Carvone, Laevo-Carvone, Caryophyllene (β-Caryophyllene), Caryophyllene oxide, Castoreum Absolute, Cedrene (α-Cedrene) (β-Cedrene), Cedrene Epoxide (α-Cedrene Epoxide), Cedrol, Cembrene, Chlorogenic Acid, Cinnamaldehyde (α-amyl-Cinnamaldehyde) (α-hexyl-Cinnamaldehyde), Cinnamic Acid, Cinnamyl Alcohol, Citronellal, Citronellol, Cryptone, Curcumene (α-Curcumene) (γ-Curcumene), Decanal, Dehydrovomifoliol, Diallyl Disulfide, Dihydroactinidiolide, Dimethyl Disulfide, Eicosane/Icosane, Elemene (β-Elemene), Estragole, Ethyl acetate, Ethyl Cinnamate, Ethyl maltol, Eucalyptol/1,8-Cineole, Eudesmol (α-Eudesmol) (β-Eudesmol) (γ-Eudesmol), Eugenol, Euphol, Farnesene, Farnesol, Fenchol (β-Fenchol), Fenchone, Geraniol, Geranyl acetate, Germacrenes, Germacrene B, Guaia-1 (10), 1 1-diene, Guaiacol, Guaiene (α-Guaiene), Gurjunene (α-Gurjunene), Herniarin, Hexanaldehyde, Hexanoic Acid, Humulene (α-Humulene) (β-Humulene), Ionol (3-oxo-α-ionol) (β-Ionol), Ionone (α-Ionone) (β-Ionone), Ipsdienol, Isoamyl acetate, Isoamyl Alcohol, Isoamyl Formate, Isoborneol, Isomyrcenol, Isopulegol, Isovaleric Acid, Isoprene, Kahweol, Lavandulol, Limonene, γ-Linolenic Acid, Linalool, Longifolene, α-Longipinene, Lycopene, Menthol, Methyl butyrate, 3-Mercapto-2-Methylpentanal, Mercaptan/Thiols, β-Mercaptoethanol, Mercaptoacetic Acid, AIM Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (β-Myrcene), γ-Muurolene, Nepetalactone, Nerol, Nerolidol, Neryl acetate, Nonanaldehyde, Nonanoic Acid, Ocimene, Octanal, Octanoic Acid, p-cymene, pentyl butyrate, phellandrene, phenylacetaldehyde, phenylethanethiol, Phenylacetic Acid, Phytol, Pinene, β-Pinene, propanethiol, Pristimerin, Pulegone, Retinol, Rutin, Sabinene, Sabinene Hydrate, cis-Sabinene Hydrate, trans-Sabinene Hydrate, Safranal, α-Selinene, α-Sinensal, β-Sinensal, β-Sitosterol, Squalene, Taxadiene, Terpin hydrate, Terpineol, Terpine-4-ol, α-Terpinene, γ-Terpinene, Terpinolene, Thiophenol, Thujone, Thymol, α-Tocopherol, Tonka Undecanone, Undecanal, Valeraldehyde/Pentanal, Verdoxan, α-Ylangene, Umbelliferone, Vanillin, a phenolic acid, a stilbenoid, a dihydroflavonol, an anthocyanin, an anthocyanidin, a polyphenol, a tannin, a flavone, flavan-3-ol, flavan-4-ol, flavan-3,4-diol flavonol, a stilbenoid, a phytochemicals, an antioxidant, a homoisoflavonoid, a phenylpropanoid, a phloroglucinol coumarin, a phenolic acid, a naphthodianthrone, a steroid glycoside, a bioflavonoid, an isoflavonoid, a neoflavonoid, adenosine, Adhyperforin, amentoflavone, Anandamide, Apigenin, Cannaflavin B, Catechin (C), Catechin 3-gallate (Cg), Chlorogenic acid, cichoric acid, caftaric acid, Daidzein, Delphinidin, Eleutherosides, epicatechin 3-gallate (ECg), Epicatechins, Epicatechin, epigallocatechin, myricetin, Oxalic acid, Pelargonidin, Tannin, Theaflavin-3-gallate, Theanine, Theobromine, Theophylline, Tryptophan, Tyramine, Xanthine, Caffeine, Cannaflavin A, Cannaflavin B, Catechin (C), Catechin 3-gallate (Cg), Epicatechin 3-gallate (ECg), Epicatechins (Epicatechin (EC)), epigallocatechin, Epigallocatechin (EGC), Epigallocatechin 3-gallate (EGCg), Gallocatechin (GC), Gallocatechin 3-gallate (GCg)), Gamma amino butyric acid, Genistein, *Ginkgo biloba*, Ginsenosides, Quercetin, Quercitrin or Rutin.

9. The method of claim 1, wherein the recombinant or genetically modified UGT can catalyze a reverse reaction to remove a sugar moiety from a glycosylated bioactive compound or a target drug.

10. The method of claim 1, wherein the recombinant or genetically modified UGT is glycosyltransferase *M. truncatula* UGT71G1has as substrates (can glycosylate) quercetin, genistein, biochanin A, hederagenin, and SN-38 (active metabolite of anti-cancer drug CPT-11 or irinotecan), and optionally (iso)flavonoids quercetin and genistein as in vitro substrates.

* * * * *